US012616399B2

(12) United States Patent
Moody et al.

(10) Patent No.: US 12,616,399 B2
(45) Date of Patent: May 5, 2026

(54) COMBINATION OF REFLECTIVE AND TRANSMISSIVE SENSORS WITH CHARACTERISTIC WAVELENGTHS FOR PHYSIOLOGICAL MONITORING

(71) Applicants:Covidien LP, Mansfield, MA (US); Hemex Health, Inc., Portland, OR (US)

(72) Inventors: Derek L. Moody, Lafayette, CO (US); Jacob D. Dove, Lafayette, CO (US); Paul S. Addison, Edinburgh (GB); Rakesh K. Sethi, Vancouver (CA); Peter M. Galen, Portland, OR (US); Linden Reustle, Milliken, CO (US)

(73) Assignees: Covidien LP, Mansfield, MA (US); Hemex Health, Inc., Portland, OR (US)

( * ) Notice: Subject to any disclaimer, the term of this patent is extended or adjusted under 35 U.S.C. 154(b) by 630 days.

(21) Appl. No.: 18/157,610

(22) Filed: Jan. 20, 2023

(65) Prior Publication Data

US 2023/0233117 A1     Jul. 27, 2023

Related U.S. Application Data

(60) Provisional application No. 63/301,814, filed on Jan. 21, 2022.

(51) Int. Cl.
A61B 5/1455          (2006.01)
A61B 5/00            (2006.01)

(52) U.S. Cl.
CPC ........ A61B 5/14552 (2013.01); A61B 5/6826 (2013.01); A61B 2562/0238 (2013.01)

(58) Field of Classification Search
CPC . A61B 5/0205; A61B 5/1455; A61B 5/14551;

A61B 5/14552; A61B 5/14553; A61B 5/14532; A61B 5/15535; A61B 5/14539; A61B 5/14542; A61B 5/14546; A61B 5/6813; A61B 5/6826

See application file for complete search history.

(56) References Cited

U.S. PATENT DOCUMENTS 6,360,113 B1 *   3/2002   Dettling ............. A61B 5/14551
                                                        600/336
6,615,065 B1 *   9/2003   Barrett ............... A61B 5/14553
                                                        600/323

(Continued)

OTHER PUBLICATIONS

Arishi et al., "Techniques for the Detection of Sickle Cell Disease: A Review", Micromachines, vol. 12, No. 519, May 5, 2021, 22 pp., doi.org/10.3390/mi12050519.

(Continued)

*Primary Examiner* — Chu Chuan Liu
(74) *Attorney, Agent, or Firm* — Dymera IP, LLC

(57) ABSTRACT

A light sensing device includes a first light source configured to emit light within a first wavelength range, a second light source configured to emit light within a second wavelength range, detector circuitry, a first photodetector in the detector circuitry configured to detect the light within the first wavelength range, and a second photodetector in the detector circuitry configured to detect the light within the second wavelength range. The first photodetector and the second photodetector are in parallel in the detector circuitry such that the detector circuitry sums electrical signals outputted by the first photodetector and the second photodetector.

16 Claims, 3 Drawing Sheets

(56)         References Cited

U.S. PATENT DOCUMENTS

| | | | | |
|---|---|---|---|---|
| 7,313,425 | B2 * | 12/2007 | Finarov | ............. A61B 5/14552 |
| | | | | 600/344 |
| 8,792,948 | B2 | 7/2014 | Segman | |
| 9,861,317 | B2 | 1/2018 | Ochs | |
| 2010/0331638 | A1 * | 12/2010 | Besko | ............... A61B 5/14552 |
| | | | | 600/323 |
| 2013/0030267 | A1 * | 1/2013 | Lisogurski | ......... A61B 5/14553 |
| | | | | 600/324 |

OTHER PUBLICATIONS

Wang et al., "HemaApp: noninvasive blood screening of hemoglobin using smartphone cameras", UbiComp '16: Proceedings of the 2016 ACM International Joint Conference on Pervasive and Ubiquitous Computing, Sep. 12, 2016, pp. 593-604, DOI: http://dx.doi.org/10.1145/2971648.2971653.

Yang et al., "Detection of wavelength in the range from ultraviolet to near infrared light using two parallel PtSe2/thin Si Schottky junctions", Mater. Horiz., vol. 8, Apr. 14, 2021, pp. 1976-1984, DOI: 10.1039/d1mh00286d.

* cited by examiner

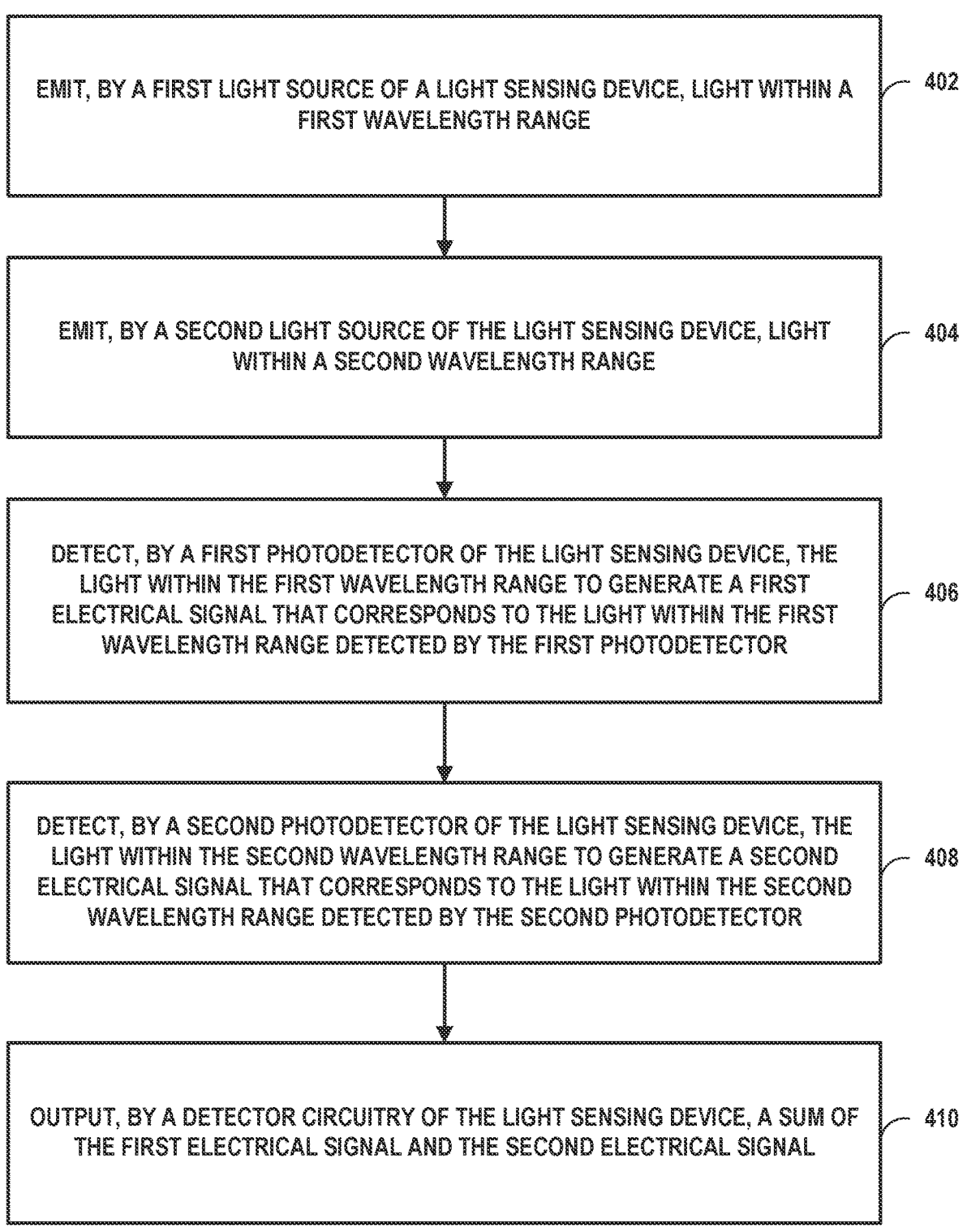

EMIT, BY A FIRST LIGHT SOURCE OF A LIGHT SENSING DEVICE, LIGHT WITHIN A FIRST WAVELENGTH RANGE — 402

EMIT, BY A SECOND LIGHT SOURCE OF THE LIGHT SENSING DEVICE, LIGHT WITHIN A SECOND WAVELENGTH RANGE — 404

DETECT, BY A FIRST PHOTODETECTOR OF THE LIGHT SENSING DEVICE, THE LIGHT WITHIN THE FIRST WAVELENGTH RANGE TO GENERATE A FIRST ELECTRICAL SIGNAL THAT CORRESPONDS TO THE LIGHT WITHIN THE FIRST WAVELENGTH RANGE DETECTED BY THE FIRST PHOTODETECTOR — 406

DETECT, BY A SECOND PHOTODETECTOR OF THE LIGHT SENSING DEVICE, THE LIGHT WITHIN THE SECOND WAVELENGTH RANGE TO GENERATE A SECOND ELECTRICAL SIGNAL THAT CORRESPONDS TO THE LIGHT WITHIN THE SECOND WAVELENGTH RANGE DETECTED BY THE SECOND PHOTODETECTOR — 408

OUTPUT, BY A DETECTOR CIRCUITRY OF THE LIGHT SENSING DEVICE, A SUM OF THE FIRST ELECTRICAL SIGNAL AND THE SECOND ELECTRICAL SIGNAL — 410

FIG. 4

COMBINATION OF REFLECTIVE AND TRANSMISSIVE SENSORS WITH CHARACTERISTIC WAVELENGTHS FOR PHYSIOLOGICAL MONITORING

This application claims the benefit of U.S. Provisional Patent Application No. 63/301,814, filed 21 Jan. 2022, the entire contents of which is incorporated herein by reference.

BACKGROUND

Hemoglobin disorders such as anemia, sickle cell, sickle cell trait, and beta thalassemia, are rare blood conditions that affect a person's hemoglobin, which is the protein in the blood that carries oxygen. Such hemoglobin disorders can be inherited conditions that may change the shape or amount of red blood cells in the body.

SUMMARY

The present disclosure describes example devices, systems, and techniques for non-invasive physiological monitoring using a light sensing device having photodetectors with ranges of wavelengths. Examples of the physiological monitoring are described with respect to sensing of hemoglobin disorders for purposes of illustration, but the example techniques are not limited to hemoglobin disorders. A light sensing device may emit various wavelengths of light that are collected by photodetectors of the light sensing device at various locations of a subject (e.g., various locations of a finger of the subject) to find the total hemoglobin of the subject, which may be used to determine whether the subject has a hemoglobin disorder. The light sensing device may sense multiple wavelengths of light to determine information that can be used to understand the water content of the arterial blood of a subject and the hemoglobin type of the subject. Such wavelengths of light may be at characteristic wavelengths for hemoglobin deficiencies, and can be used to determine disease states of such deficiencies.

For example, the light sensing device may emit light at ultraviolet (UV) or near-UV wavelengths, which are characteristic wavelengths that are around the global maxima or minima of the hemoglobin absorption spectra. The signals from such wavelengths may be used to compare water absorption to hemoglobin absorption for a total hemoglobin measurement. Additionally, the signals from such wavelengths may also be used to sense changes to the pH or hypoxia in the blood of the subject, which may be due to certain hemoglobinopathies like sickle cell anemia. These changes in the absorption spectra of hemoglobin and may be sensed using these shorter wavelengths.

Shorter wavelengths present a higher noise based on pigmentation because of the absorption spectrum of melanin. As such, the light sensing device may also emit light at infrared (IR) wavelengths, which can be used to reduce the effect of skin pigmentation on the signal as the absorption spectra of melanin is lower at longer wavelengths. In addition, water may dominate the absorption at these longer wavelengths, so the IR wavelengths may be used to compare the absorption of water versus hemoglobin to create a total hemoglobin measurement.

The light sensing device may concurrently measure the transmission and reflectance of the wavelengths of light using a set of detectors that are in parallel. Specifically, the light sensing device may use multiple photodetectors with different responsivities. The multiple photodetectors may be placed in parallel in the same circuit to allow multiple photodetectors with different responsivities to add current to the same circuit, and the current outputted by the multiple photodetectors can be sent for amplification. For example, the output nodes of the multiple photodetectors may be connected together at a common node. The current at the common node may be equivalent to the sum of the current outputted by the multiple photodetectors since the output nodes of the multiple photodetectors are connected at the common node.

In some examples, photodetectors are located at multiple locations in the light sensing device. Specifically, one or more photodetectors may be located in in a shorter optical path length reflective position of the light sensing device, and one or more photodetectors may be placed in a longer optical path length transmission position of the light sensing device. The difference in these long and short optical path lengths may be used to improve the signal quality of the signals outputted by the photodetectors and to remove noise factors from such signals. For example, the signals outputted by the one or more photodetectors in the shorter path length reflective position could be used to characterize the superficial tissue and to account for pigmentation, interstitial fluid, or other potential confounders, while the signals outputted by the one or more photodetectors in the longer path length transmission position may be used to generate the final measurement after accounting for such noise factors.

In some aspects, the techniques described herein relate to a light sensing system including: a first light source configured to emit light within a first wavelength range; a second light source configured to emit light within a second wavelength range; a first photodetector configured to detect the light within the first wavelength range; a second photodetector configured to detect the light within the second wavelength range, wherein the first photodetector and the second photodetector are in parallel; and detector circuitry configured to sum electrical signals outputted by the first photodetector and the second photodetector.

In some aspects, the techniques described herein relate to a method including: emitting, by a first light source of a light sensing device, light within a first wavelength range; emitting, by a second light source of the light sensing device, light within a second wavelength range; detecting, by a first photodetector of the light sensing device, the light within the first wavelength range to generate a first electrical signal that corresponds to the light within the first wavelength range detected by the first photodetector; detecting, by a second photodetector of the light sensing device, the light within the second wavelength range to generate a second electrical signal that corresponds to the light within the second wavelength range detected by the second photodetector; and outputting, by a detector circuitry of the light sensing device, a sum of the first electrical signal and the second electrical signal.

In some aspects, the techniques described herein relate to an apparatus including: means for emitting light within a first wavelength range; means for emitting light within a second wavelength range; means for detecting the light within the first wavelength range to generate a first electrical signal that corresponds to the light within the first wavelength range; means for detecting the light within the second wavelength range to generate a second electrical signal that corresponds to the light within the second wavelength range; and means for outputting a sum of the first electrical signal and the second electrical signal.

The details of one or more examples are set forth in the accompanying drawings and the description below. Other features, objects, and advantages will be apparent from the description and drawings, and from the claims.

BRIEF DESCRIPTION OF THE DRAWINGS

FIG. 4 is a flow diagram illustrating example operations of an example light sensing device.

DETAILED DESCRIPTION

Figure 1:
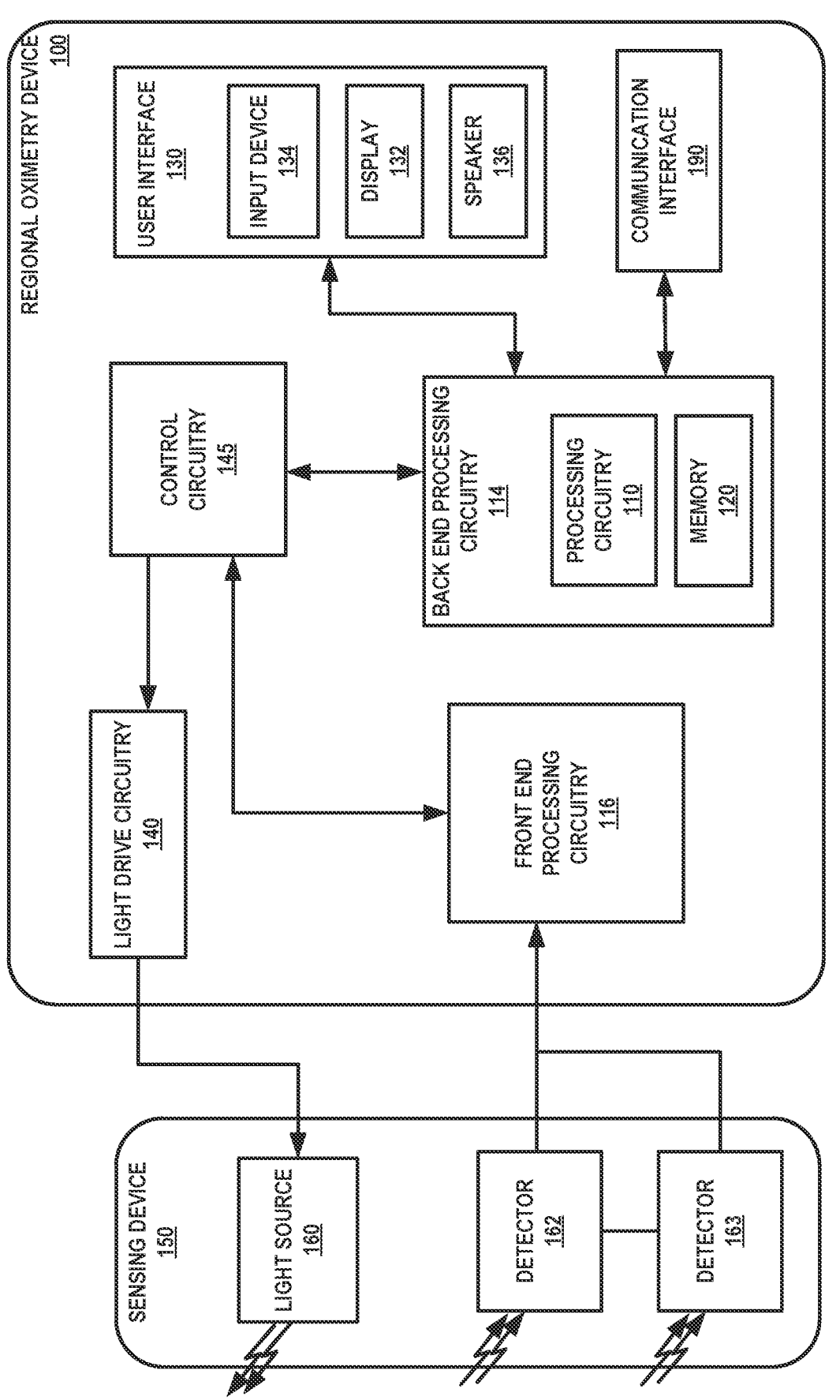
FIG. 1 is a conceptual block diagram illustrating an example regional oximetry system, in accordance with aspects of this disclosure.

FIG. 1 is a conceptual block diagram illustrating an example regional oximetry system, in accordance with aspects of this disclosure. In the example shown in FIG. 1, regional oximetry device 100 is coupled to sensing device 150 and may be collectively referred to as a regional oximetry system, which each generate and process physiological signals of a subject. In some examples, sensing device 150 and regional oximetry device 100 may be part of an oximeter. As shown in FIG. 1, regional oximetry device 100 includes back-end processing circuitry 114, user interface 130, light drive circuitry 140, front-end processing circuitry 116, control circuitry 145, and communication interface 190. Regional oximetry device 100 may be communicatively coupled to sensing device 150.

Sensing device 150 may be configured to be placed on the skin of a subject to determine regional oxygen saturation of a particular tissue region. In the example shown in FIG. 1, sensing device 150 includes light source 160, detector 162, and detector 163. In some examples, sensing device 150 may include more than two detectors. Light source 160 may also be referred to as an emitter and may include two or more light emitting diodes (LEDs) each configured to emit photonic signals at different wavelengths of light, e.g., red or near infrared (IR) light into a subject's tissue.

As used herein, the term "light" may refer to energy produced by radiative sources and may include one or more of ultrasound, radio, microwave, millimeter wave, infrared, visible, near ultraviolet, ultraviolet, gamma ray or X-ray electromagnetic radiation. Light may also include any wavelength within the radio, microwave, infrared, visible, ultraviolet, or X-ray spectra, and that any suitable wavelength of electromagnetic radiation may be appropriate for use with the present techniques. Detectors 162 and 163 may be chosen to be specifically sensitive to the chosen targeted energy spectrum of light source 160.

In accordance with aspects of the present disclosure, light source 160 may include two or more light sources: an ultraviolet or near ultraviolet light emitting light source and an infrared (IR) light emitting light source for emitting light into the tissue to a subject to generate physiological signals. In some examples, the ultraviolet or near ultraviolet light emitting light source may emit light having a wavelength of between about 300 nanometers (nm) and about 550 nm, which are characteristic wavelengths that are around the global maxima or minima of the hemoglobin absorption spectra, and the IR light emitting light source may emit light having a wavelength of between about 1300 nm and about 1500 nm, which can be used to reduce the effect of skin pigmentation on the signal as the absorption spectra of melanin is lower at longer wavelengths. Additionally, water dominates the absorption at these longer wavelengths so these wavelengths could also be used to compare the absorption of water versus hemoglobin to create a total hemoglobin measurement. Other wavelengths of light may be used in other examples. Other wavelengths of light may be used in other examples, and light source 160 may include any number of light sources with any suitable characteristics.

In some examples, multiple light sources similar to light source 160 may be placed at multiple locations within sensing device 150. In some examples, the light sources may be switched on separately, such as in a sequential pattern or any other pattern, so that sensing device may make separate physiological measurement of a patient based on the different light sources being switched on.

In order to detect light across such a broad spectrum of wavelengths from about 300 nm of light to about 1,500 nm of light, sensing device 150 may include multiple detectors with different responsivities. In the example of FIG. 1, sensing device 150 includes detectors 162 and 163 having respective different responsivities to wavelengths of light. For example, detector 162 may be photodetector configured to detect the intensity of light at ultraviolet or near ultraviolet light wavelengths of between about 300 nanometers (nm) and about 550 nm, while detector 163 may be a photodetector configured to detect the intensity of light at IR wavelengths of between about 1300 nm and about 1500 nm.

In operation, light may enter detector 162 after passing through the subject's tissue, including skin, bone, and other shallow tissue (e.g., non-cerebral tissue and shallow cerebral tissue). Light may enter detector 163 after passing through the subject's tissue, including skin, bone, other shallow tissue (e.g., non-cerebral tissue and shallow cerebral tissue), and deep tissue (e.g., deep cerebral tissue). Detectors 162 and 163 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detectors 162 and 163.

In some examples, detectors 162 and 163 are placed in parallel within the same detector circuit in the circuitry of light sensing device 150. Placing detectors having different light responsivities, such as detectors 162 and 163, in parallel in a detector circuit may enable the detector circuit to add together the electrical current outputted by detectors 162 and 163 and to send the sum of the electrical current from detectors 162 and 163 to front end regional oximetry device 100 for, e.g., amplification.

In some examples, detectors 162 and 163 are just one pair of a plurality of pairs of photodetectors in light sensing device 150. That is, light sensing device 150 may include multiple sets of photodetectors located at different locations of light sensing device 150, where each set of detectors includes multiple photodetectors with different responsivities, such as detectors 162 and 163, including a first detector configured to detect the intensity of light at ultraviolet or near ultraviolet light wavelengths of between about 300 nm and about 550 nm and a second detector configured to detect the intensity of light at IR wavelengths of between about 1300 nm and about 1500 nm. Similar to detectors 162 and 163, a set of two detectors with different responsivities may be placed in parallel in the same detector circuit in the circuitry of light sensing device 150, so that light sensing device 150 may send the sum of the electrical current from detectors 162 and 163 to front end regional oximetry device 100.

In some examples, a first set of two detectors with different responsivities, such as detectors 162 and 163, may be placed in a shorter optical path length reflective position in light sensing device 150, and a second set of two detectors with different responsivities may be placed in a longer optical path length transmission position in light sensing device 150. The difference in these long and short optical path lengths could be used to improve the signal outputted by the detectors 162, 163 and to remove noise factors from such signals. For example, the short path length signal outputted by the first set of two detectors placed in the shorter path length reflective position may be used to characterize the superficial tissue, and hence account for pigmentation, interstitial fluid, or other potential confounders, while the signal from the second set of two detectors placed in the longer path length transmission position may be used to generate a final measurement after accounting for noise factors.

After converting the received light to an electrical signal, detectors 162 and 163 may send the detection signals to regional oximetry device 100, where the detection signals may be processed and physiological parameters may be determined (e.g., based on the absorption of the red and IR wavelengths in the subject's tissue at both detectors). In some examples, one or more of the detection signals may be preprocessed by sensing device 150 before being transmitted to regional oximetry device 100. Additional example details of determining oxygen saturation based on light signals may be found in commonly assigned U.S. Pat. No. 9,861,317, which issued on Jan. 9, 2018, and is entitled "Methods and Systems for Determining Regional Blood Oxygen Saturation," the entire content of which is incorporated herein by reference.

Control circuitry 145 may be coupled to light drive circuitry 140, front-end processing circuitry 116, and back-end processing circuitry 114, and may be configured to control the operation of these components. In some examples, control circuitry 145 may be configured to provide timing control signals to coordinate their operation of light drive circuitry 140, front-end processing circuitry 116, and back-end processing circuitry 114. For example, light drive circuitry 140 may generate one or more light drive signals, which may be used to turn on and off light source 160, based on the timing control signals provided by control circuitry 145. Front-end processing circuitry 116 may use the timing control signals to operate synchronously with light drive circuitry 140. For example, front-end processing circuitry 116 may synchronize the operation of an analog-to-digital converter and a demultiplexer with the light drive signal based on the timing control signals. In addition, the back-end processing circuitry 114 may use the timing control signals to coordinate its operation with front-end processing circuitry 116.

Light drive circuitry 140, as discussed above, may be configured to generate a light drive signal that is provided to light source 160 of sensing device 150. The light drive signal may, for example, control the intensity of light source 160 and the timing of when light source 160 is turned on and off. In some examples, light drive circuitry 140 provides one or more light drive signals to light source 160. Where light source 160 is configured to emit two or more wavelengths of light, the light drive signal may be configured to control the operation of each wavelength of light. The light drive signal may comprise a single signal or may comprise multiple signals (e.g., one signal for each wavelength of light).

Front-end processing circuitry 116, back-end processing circuitry 114, and processing circuitry 110, as well as other processors, processing circuitry, controllers, control circuitry, and the like, described herein, may include one or more processors, and may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, front-end processing circuitry 116, back-end processing circuitry 114, and processing circuitry 110 may include multiple components, such as any combination of one or more microprocessors, one or more DSPs, one or more ASICs, or one or more FPGAs, as well as other discrete or integrated logic circuitry, and/or analog circuitry.

Front-end processing circuitry 116 may perform any suitable analog conditioning of the detector signals. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. The conditioned analog signals may be processed by an analog-to-digital converter of circuitry 116, which may convert the conditioned analog signals into digital signals. Front-end processing circuitry 116 may operate on the analog or digital form of the detector signals to separate out different components of the signals. Front-end processing circuitry 116 may also perform any suitable digital conditioning of the detector signals, such as low pass, high pass, band pass, notch, averaging, or any other suitable filtering, amplifying, performing an operation on the signal, performing any other suitable digital conditioning, or any combination thereof. Front-end processing circuitry 116 may decrease the number of samples in the digital detector signals. In some examples, front-end processing circuitry 116 may also remove dark or ambient contributions to the received signal.

Back-end processing circuitry 114 may include processing circuitry 110 and memory 120. Processing circuitry 110 may include an assembly of analog or digital electronic components and may be configured to execute software, which may include an operating system and one or more applications, as part of performing the functions described herein with respect to, e.g., processing circuitry 110. Processing circuitry 110 may receive and further process one or more signals received from front-end processing circuitry 116. For example, processing circuitry 110 may determine physiological parameter values based on the received signals. For example, processing circuitry 110 may compute one or more of regional oxygen saturation, blood oxygen saturation (e.g., arterial, venous, or both), pulse rate, respiration rate, respiration effort, blood pressure, hemoglobin concentration (e.g., oxygenated, deoxygenated, and/or total), any other suitable physiological parameters, or any combination thereof.

Processing circuitry 110 may perform any suitable signal processing of a signal, such as any suitable band-pass filtering, adaptive filtering, closed-loop filtering, any other suitable filtering, and/or any combination thereof. Processing circuitry 110 may also receive input signals from additional sources not shown. For example, processing circuitry 110 may receive an input signal containing information about treatments provided to the subject from user interface 130. Additional input signals may be used by processing circuitry 110 in any of the determinations or operations it performs in accordance with back-end processing circuitry 114 or regional oximetry device 100.

Processing circuitry 110 is configured to perform the techniques of this disclosure. For example, processing circuitry 110 is configured to receive signals outputted by sensing device 150, which may be processed (e.g., amplified) by front-end processing circuitry 116. Processing circuitry 110 is configured to determine, based on the signals outputted by sensing device 150, the total hemoglobin of a subject, the water content of the arterial blood of the subject, the hemoglobin type of the subject, and the like, to determine whether the subject is suffering from one or more hemoglobin disorders of a subject.

Memory 120 may include any suitable computer-readable media capable of storing information that can be interpreted by processing circuitry 110. In some examples, memory 120 may store program instructions that are executable by processing circuitry 110. When executed by processing circuitry 110, such program instructions may cause processing circuitry 110 to provide the functionality ascribed to it herein. The program instructions may be embodied in software, firmware, and/or RAMware. Memory 120 may include any one or more of volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

In some examples, memory 120 may store measurements of physiological parameters, mean arterial pressure values, oxygen saturation values, correlation coefficient values, threshold rates, threshold values, threshold time durations, blood pressure variation values, predetermined ranges of variation, maximum and minimum blood pressure values, threshold rates, non-bypass conditions, and kernels, any other determined values, or any combination thereof, in a memory device for later retrieval. Back-end processing circuitry 114 may be communicatively coupled with user interface 130 and communication interface 190.

User interface 130 may include input device 134, display 131, and/or speaker 136, which may be any suitable audio device including circuitry and configured to generate and output a noise. In some examples, user interface 130 may include fewer or additional components. User interface 130 is configured to present information to a user (e.g., a clinician). For example, user interface 130 and/or display 131 may include a monitor, cathode ray tube display, a flat panel display such as a liquid crystal (LCD) display, a plasma display, a light emitting diode (LED) display, and/or any other suitable display. In some examples, user interface 130 may be part of a multiparameter monitor (MPM) or other physiological signal monitor used in a clinical or other setting, a personal digital assistant, mobile phone, tablet computer, laptop computer, any other suitable computing device, or any combination thereof, with a built-in display or a separate display.

User interface 130 may include, for example, any suitable device such as one or more medical devices (e.g., a medical monitor that displays various physiological parameters, a medical alarm, or any other suitable medical device that either displays physiological parameters or uses the output of back-end processing circuitry 114 as an input), one or more display devices (e.g., monitor, personal digital assistant (PDA), mobile phone, tablet computer, clinician workstation, any other suitable display device, or any combination thereof), one or more audio devices, one or more memory devices, one or more printing devices, any other suitable output device, or any combination thereof.

Input device 134 may include any type of user input device such as a keyboard, a mouse, a touch screen, buttons, switches, a microphone, a joy-stick, a touch pad, or any other suitable input device or combination of input devices. In other examples, input device 134 may be a pressure-sensitive or presence-sensitive display that is included as part of display 131. Input device 134 may also receive inputs to select a model number of sensing device 150 or other equipment. In some examples, processing circuitry 110 may determine a threshold rate and/or a length of a window of time based on user input received from input device 134.

In some examples, the subject may be a medical patient and display 131 may exhibit a list of values which may generally apply to the subject, such as, for example, an oxygen saturation signal indicator, a blood pressure signal indicator, a COx signal indicator, a COx value indicator, and/or an autoregulation status indicator. Display 131 may also be configured to present additional physiological parameter information. Additionally, display 131 may present, for example, one or more estimates of a subject's regional oxygen saturation generated by regional oximetry device 100 (referred to as an "rSO2" measurement). Display 131 may also present indications of the upper and lower limits of autoregulation. Speaker 136 within user interface 130 may provide an audible sound that may be used in various examples, such as for example, sounding an audible alarm in the event that the autoregulation status of a patient is impaired or that the patient's physiological parameters are not within a predefined normal range.

Communication interface 190 may enable regional oximetry device 100 to exchange information with external devices. Communication interface 190 may include any suitable hardware, software, or both, which may allow regional oximetry device 100 to communicate with electronic circuitry, a device, a network, a server or other workstations, a display, or any combination thereof. For example, regional oximetry device 100 may receive MAP values and/or oxygen saturation values from an external device via communication interface 190.

The components of regional oximetry device 100 that are shown and described as separate components are shown and described as such for illustrative purposes only. In some examples the functionality of some of the components may be combined in a single component. For example, the functionality of front-end processing circuitry 116 and back-end processing circuitry 114 may be combined in a single processor system. Additionally, in some examples the functionality of some of the components of regional oximetry device 100 shown and described herein may be divided over multiple components. For example, some or all of the functionality of control circuitry 145 may be performed in front-end processing circuitry 116, in back-end processing circuitry 114, or both. In other examples, the functionality of one or more of the components may be performed in a different order or may not be required. In some examples, all of the components of regional oximetry device 100 can be realized in processor circuitry.

Figure 2:
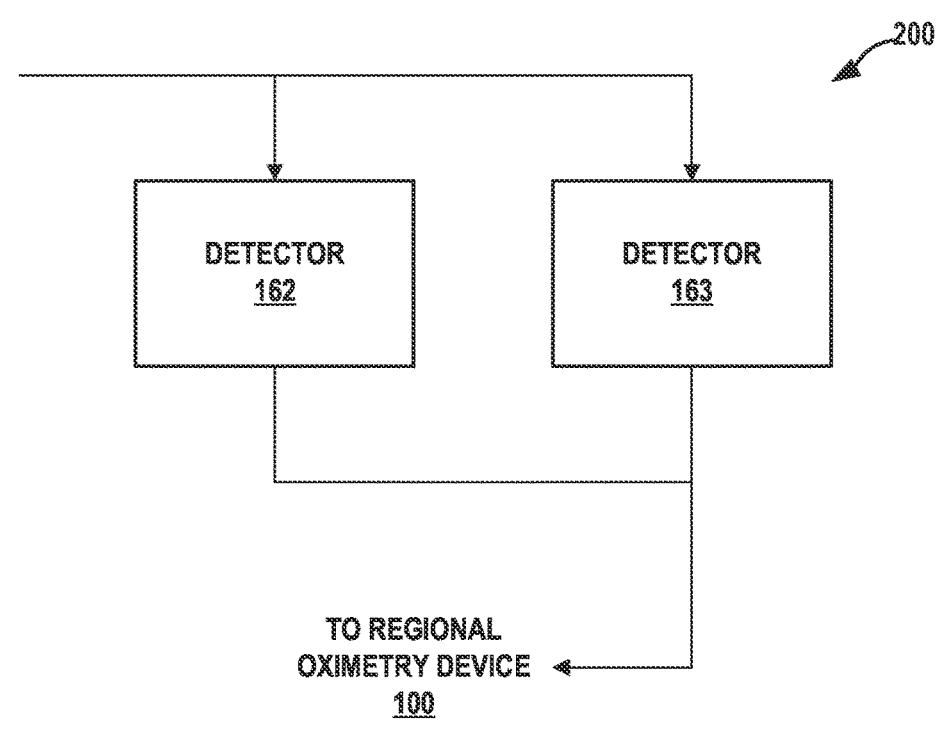
FIG. 2 illustrates an example detector circuit of the light sensing device of FIG. 1, in accordance with aspects of this disclosure.

FIG. 2 illustrates an example detector circuitry 200 of the light sensing device 150 of FIG. 1, in accordance with aspects of this disclosure. As shown in FIG. 2, detector circuitry 200 may be an example portion of the circuitry of light sensing device 150 of FIG. 1. As shown in FIG. 2, detector circuitry 200 includes detector 162 and detector 163 that are placed in parallel within the detector circuitry 200. Because detectors 162 and 163 are in parallel in detector circuitry 200, the electrical current outputted by detectors 162 and 163 are added together and sent from detector circuitry 200 to front end regional oximetry device 100 for, e.g., amplification.

As can be seen in FIG. 2, detector 162 is a first output node and detector 163 is a second output node. When detectors 162 and 163 are in parallel in detector circuitry 200, the first output node and the second output node are electrically connected to one another at a common node, such that detector circuitry 200 outputs the summed electrical current from detectors 162 and 163 by receiving and/or outputting the summed electrical current from the common node.

Figure 3:
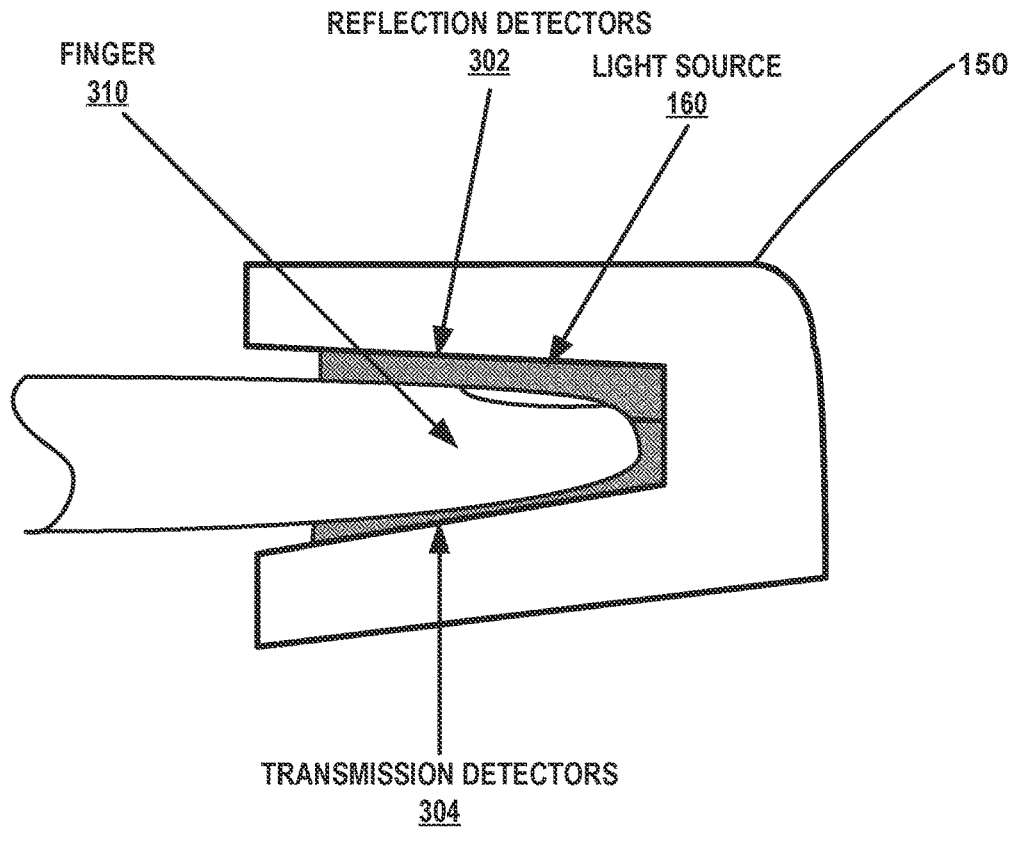
FIG. 3 illustrates the light sensing device of FIG. 1, in accordance with aspects of this disclosure.

FIG. 3 illustrates the light sensing device 150 of FIG. 1, in accordance with aspects of this disclosure. As shown in FIG. 3, light sensing device 150 may include light source 160 and detectors 302 and 304 and may be placed around a finger 310 of a subject.

Detectors 302 may include a set of two detectors similar to detectors 162 and 163 of FIG. 1. That is, detectors 302 may include a first detector configured to detect the intensity of light at ultraviolet or near ultraviolet light wavelengths of between about 300 nanometers (nm) and about 550 nm and a second configured to detect the intensity of light at IR wavelengths of between about 1300 nm and about 1500 nm, where the two detectors of detectors 302 are placed in parallel within the same detector circuit to enable the detector circuit to add together the electrical current outputted by the two detectors and to send the sum of the electrical current from the two detectors to regional oximetry device 100.

Similarly, detector 304 may also include a set of two detectors similar to detectors 162 and 163 of FIG. 1. That is, detectors 304 may include a first detector configured to detect the intensity of light at ultraviolet or near ultraviolet light wavelengths of between about 300 nanometers (nm) and about 550 nm and a second configured to detect the intensity of light at IR wavelengths of between about 1300 nm and about 1500 nm, where the two detectors of detectors 304 are placed in parallel within the same detector circuit to enable the detector circuit to add together the electrical current outputted by the two detectors and to send the sum of the electrical current from the two detectors to regional oximetry device 100.

In the example of FIG. 3, detectors 302 are placed in a shorter optical path length reflective position in light sensing device 150, and are therefore also referred to as reflection detectors, and detectors 304 are placed in a longer optical path length transmission position in light sensing device 150, and are therefore also referred to as transmission detectors. That is, detector 302 is located on the same side of finger 310 as light source 160, to sense light reflected by finger 310. Meanwhile, detectors 304 is located directly opposite of detectors 302 on the other side of finger 310 from detectors 302 and light source 160, to sense light transmitted through finger 310.

The difference in these long and short optical path lengths may be used to improve the signal outputted by the detectors and to remove noise factors from such signals. For example, the short path length signal outputted by detectors 302 placed in the shorter optical path length reflective position may be used to characterize the superficial tissue, and hence account for pigmentation, interstitial fluid, or other potential confounders, while the signal from detectors 304 placed in the longer optical path length transmission position may be used to generate a final measurement after accounting for noise factors.

FIG. 4 is a flow diagram illustrating example operations of an example light sensing device. Although FIG. 4 is described with respect to light sensing device 150 (FIG. 1), in other examples, different light sensing devices may perform any part of the technique of FIG. 4.

The technique illustrated in FIG. 4 includes emitting, by a first light source of a light sensing device 150, light within a first wavelength range (402). The technique further includes emitting, by a second light source of the light sensing device 150, light within a second wavelength range (404). The technique further includes detecting, by a first photodetector 162 of the light sensing device 150, the light within the first wavelength range to generate a first electrical signal that corresponds to the light within the first wavelength range detected by the first photodetector 162 (406). The technique further includes detecting, by a second photodetector 163 of the light sensing device 150, the light within the second wavelength range to generate a second electrical signal that corresponds to the light within the second wavelength range detected by the second photodetector 163 (408). The technique further includes outputting, by a detector circuitry 200 of the light sensing device 150, a sum of the first electrical signal and the second electrical signal (410).

In some examples, the detector circuitry 200 includes the first photodetector 162 and the second photodetector 163, where the first photodetector 162 and the second photodetector 163 are in parallel, and the detector circuitry 200 may sum the electrical signals outputted by the first photodetector 162 and the second photodetector 163.

In some examples, the first photodetector 162 comprises a first output node and the second photodetector 163 comprises a second output node, where the first photodetector 162 and the second photodetector 163 being in parallel includes the first output node and the second output node being electrically connected to one another at a common node, and where the detector circuitry 200 may perform at least one of: receiving or outputting a summed electrical signal from the common node.

In some examples, the first light source is a near ultraviolet light emitting light source, and the second light source is an infrared light emitting light source.

In some examples, the first wavelength range is between about 300 nanometers (nm) and about 550 nm, and the second wavelength range is between about 1300 nm and 1500 nm.

In some examples, light sensing device 150 further includes a third photodetector in the detector circuitry 200 configured to detect the light within the first wavelength range and a fourth photodetector in the detector circuitry 200 configured to detect the light within the second wavelength range, where the detector circuitry 200 is configured to sum electrical signals outputted by the third photodetector and the fourth photodetector.

In some examples, the first photodetector 162 and the second photodetector 163 are disposed in a shorter optical path length reflective position in the light sensing device 150, and the third photodetector and the fourth photodetector are disposed in a longer optical path length transmission position in the light sensing device 150.

In some examples, the detector circuitry 200 may output a sum of the electrical signals outputted by the first photodetector 162 and the second photodetector 163 to a regional oximetry device 100.

Aspects of this disclosure include the following examples.

Example 1. A light sensing system comprising: a first light source configured to emit light within a first wavelength range; a second light source configured to emit light within a second wavelength range; a first photodetector configured to detect the light within the first wavelength range; a second photodetector configured to detect the light within the second wavelength range, wherein the first photodetector and the second photodetector are in parallel; and detector circuitry configured to sum electrical signals outputted by the first photodetector and the second photodetector.

Example 2. The light sensing system of example 1, wherein the detector circuitry comprises the first photodetector and the second photodetector, and wherein the first photodetector and the second photodetector are in parallel, such that the detector circuitry is configured to sum the electrical signals outputted by the first photodetector and the second photodetector.

Example 3. The light sensing system of any of examples 1 and 2, wherein the first photodetector comprises a first output node and the second photodetector comprises a second output node, wherein the first photodetector and the second photodetector being in parallel comprises the first output node and the second output node being electrically connected to one another at a common node, and wherein the detector circuitry configured to sum the electrical signals outputted by the first photodetector and the second photodetector is further configured to perform at least one of: receiving or outputting a summed electrical signal from the common node.

Example 4. The light sensing system of any of examples 1-3, wherein: the first light source is a near ultraviolet light emitting light source; and the second light source is an infrared light emitting light source.

Example 5. The light sensing system of any of examples 1-4, wherein: the first wavelength range is between about 300 nanometers (nm) and about 550 nm; and the second wavelength range is between about 1300 nm and 1500 nm.

Example 6. The light sensing system of any of examples 1-3, further comprising: a third photodetector in the detector circuitry configured to detect the light within the first wavelength range; and a fourth photodetector in the detector circuitry configured to detect the light within the second wavelength range; wherein the detector circuitry is configured to sum electrical signals outputted by the third photodetector and the fourth photodetector.

Example 7. The light sensing system of example 6, wherein: the first photodetector and the second photodetector are disposed in a shorter optical path length reflective position in the light sensing system; and the third photodetector and the fourth photodetector are disposed in a longer optical path length transmission position in the light sensing system.

Example 8. The light sensing system of any of examples 1-7, wherein the detector circuitry is configured to output a sum of the electrical signals outputted by the first photodetector and the second photodetector to a regional oximetry device.

Example 9. A method comprising: emitting, by a first light source of a light sensing device, light within a first wavelength range; emitting, by a second light source of the light sensing device, light within a second wavelength range; detecting, by a first photodetector of the light sensing device, the light within the first wavelength range to generate a first electrical signal that corresponds to the light within the first wavelength range detected by the first photodetector; detecting, by a second photodetector of the light sensing device, the light within the second wavelength range to generate a second electrical signal that corresponds to the light within the second wavelength range detected by the second photodetector; and outputting, by a detector circuitry of the light sensing device, a sum of the first electrical signal and the second electrical signal.

Example 10. The method of example 9, wherein the first photodetector and the second photodetector are in parallel in the detector circuitry.

Example 11. The method of any of examples 9 and 10, wherein: the first light source is a near ultraviolet light emitting light source; and the second light source is an infrared light emitting light source.

Example 12. The method of any of examples 9-11, wherein: the first wavelength range is between about 300 nanometers (nm) and about 550 nm; and the second wavelength range is between about 1300 nm and 1500 nm.

Example 13. The method of any of examples 9-12, further comprising: detecting, by a third photodetector of the light sensing device, the light within the first wavelength range to generate a third electrical signal that corresponds to the light within the first wavelength range detected by the third photodetector; detecting, by a fourth photodetector of the light sensing device, the light within the second wavelength range to generate a fourth electrical signal that corresponds to the light within the second wavelength range detected by the fourth photodetector; and outputting, by the detector circuitry of the light sensing device, a sum of the third electrical signal and the fourth electrical signal.

Example 14. The method of example 13, wherein the third photodetector and the fourth photodetector are in parallel in the detector circuitry 200.

Example 15. The method of any of examples 13 and 14, wherein: the first photodetector and the second photodetector are disposed in a shorter optical path length reflective position in the light sensing device; and the third photodetector and the fourth photodetector are disposed in a longer optical path length transmission position in the light sensing device.

Example 16. The method of any of examples 9-15, wherein outputting the sum of the first electrical signal and the second electrical signal further comprises: outputting, by the detector circuitry of the light sensing device, the sum of the first electrical signal and the second electrical signal to a regional oximetry device.

Example 17. A device configured to perform any combination of the method of examples 9-16.

Example 18. An apparatus comprising means for performing any combination of the method of examples 9-16.

The techniques described in this disclosure, including those attributed to device 100, processing circuitry 110, control circuitry 122, sensing circuitries 140, 142, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices. Processing circuitry, control circuitry, and sensing circuitry, as well as other processors and controllers described herein, may be implemented at least in part as, or include, one or more executable applications, application modules, libraries, classes, methods, objects, routines, subroutines, firmware, and/or embedded code, for example.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. The computer-readable medium may be an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

The functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements.

Various examples of the disclosure have been described. Any combination of the described systems, operations, or functions is contemplated. These and other examples are within the scope of the following claims.

What is claimed is:

1. A light sensing system comprising:
a first light source configured to emit light within a first wavelength range;
a second light source configured to emit light within a second wavelength range;
a first pair of photodetectors located in a reflective position with respect to the first and second light sources, the first pair of photodetectors comprising a first photodetector and a second photodetector having different responsivities to wavelengths of light, wherein the first photodetector is configured to detect the light within the first wavelength range and the second photodetector is configured to detect the light within the second wavelength range;
a second pair of photodetectors located in a transmission position with respect to the first and second light sources, the second pair of photodetectors comprising a third photodetector and a fourth photodetector having different responsivities to wavelengths of light, wherein the third photodetector is configured to detect the light within the first wavelength range and the fourth photodetector is configured to detect the light within the second wavelength range, wherein the first photodetector and the second photodetector are in parallel with each other and wherein the third and fourth photodetectors are in parallel with each other; and
detector circuitry configured to:

sum electrical signals outputted by the first photodetector and the second photodetector;
sum electrical signals outputted by the third photodetector and the fourth photodetector; and
output the summed signals to a regional oximetry device.

2. The light sensing system of claim 1, wherein the first photodetector comprises a first output node and the second photodetector comprises a second output node, wherein the first photodetector and the second photodetector being in parallel comprises the first output node and the second output node being electrically connected to one another at a common node, and wherein the detector circuitry configured to sum the electrical signals outputted by the first photodetector and the second photodetector is further configured to perform at least one of receiving or outputting a summed electrical signal from the common node.

3. The light sensing system of claim 1, wherein:
the first light source is a near ultraviolet light emitting light source; and
the second light source is an infrared light emitting light source.

4. The light sensing system of claim 1, wherein:
the first wavelength range is between about 300 nanometers (nm) and about 550 nm; and
the second wavelength range is between about 1300 nm and 1500 nm.

5. The light sensing system of claim 1, wherein, relative to each other:
the reflective position comprises a shorter optical path length in the light sensing system; and
the transmission position comprises a longer optical path length in the light sensing system.

6. The light sensing system of claim 1, wherein the first light source and the second light source are switched on separately according to a sequential pattern.

7. A method comprising:
emitting, by a first light source of a light sensing device, light within a first wavelength range;
emitting, by a second light source of the light sensing device, light within a second wavelength range;
detecting, by a first pair of photodetectors, the light within the first wavelength range and the light within the second wavelength range through a reflective optical path, wherein detecting by the first pair of photodetectors comprises generating a first electrical signal that corresponds to light within the first wavelength range and generating a second electrical signal that corresponds to light within the second wavelength range;
detecting, by a second pair of photodetectors, the light within the first wavelength range and the light within the second wavelength range through a transmission optical path, wherein the transmission optical path is longer than the reflective optical path, and wherein detecting by the second pair of photodetectors comprises generating a third electrical signal that corresponds to light within the first wavelength range and generating a fourth electrical signal that corresponds to light within the second wavelength range;
summing, by the light sensing device, the first electrical signal and the second electrical signal;
summing, by the light sensing device, the third electrical signal and the fourth electrical signal; and
outputting, by the light sensing device, the summed signals to a regional oximetry device.

8. The method of claim 7, wherein the first pair of photodetectors comprises a first photodetector and a second photodetector in parallel and wherein the second pair of photodetectors comprises a third photodetector and a fourth photodetector in parallel.

9. The method of claim 7, wherein:

the first light source is a near ultraviolet light emitting light source; and the second light source is an infrared light emitting light source.

10. The method of claim 7, wherein:

the first wavelength range is between about 300 nanometers (nm) and about 550 nm; and the second wavelength range is between about 1300 nm and 1500 nm.

11. The method of claim 7, wherein emitting, by the first light source of the light sensing device, the light within the first wavelength range and emitting, by the second light source of the light sensing device, the light within the second wavelength range further comprises separately emitting the light within the first wirelength range and the light within the second wirelength range according to a sequential pattern.

12. The method of claim 7, wherein the first pair of photodetectors comprises first and second photodetectors and the second pair of photodetectors comprises third and fourth photodetectors, and wherein the first photodetector has a wavelength responsivity that differs from the second photodetector, and wherein the third photodetector has a wavelength responsivity that differs from the fourth photodetector.

13. The method of claim 12, wherein the first and third photodetectors are responsive to the light within the first wavelength range, and wherein the second and fourth photodetectors are responsive to the light within the second wavelength range.

14. The method of claim 7, further comprising determining, by the regional oximetry device, a physiological parameter of the patient based on the summed signals.

15. The method of claim 14, wherein the physiological parameter comprises oxygen saturation.

16. The method of claim 14, wherein the physiological parameter comprises hemoglobin concentration.

* * * * *